Figure 1:
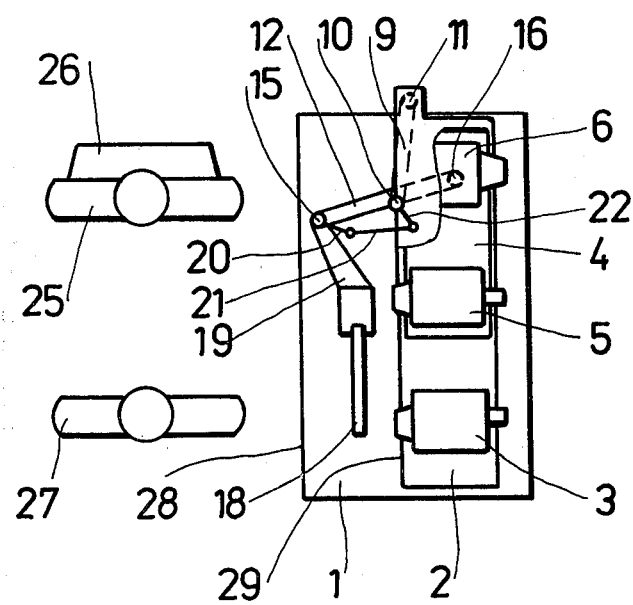

United States Patent [19]

Schön et al.

[11] 4,421,394
[45] Dec. 20, 1983

[54] DISPLACEMENT SYSTEM FOR AN OPTHALMOLOGIC EXAMINATION UNIT

[76] Inventors: Romuald Schön, 5, Werner-Seelenbinder-Str., Jena-Lobeda, District of Gera; Manfred Doms, 5, Zenkerweg; Peter Vorberg, 35, Luise-Seidler-Str., both of Jena, District of Gera; Horst Schröter, 13, Bibraer-Landstr., Kahla, District of Gera, all of German Democratic Rep.

[21] Appl. No.: 330,679

[22] Filed: Dec. 22, 1981

[30] Foreign Application Priority Data

Mar. 13, 1981 [DD] German Democratic Rep. ... 228421

[51] Int. Cl.³ .............................................. A61B 3/00
[52] U.S. Cl. ................................... 351/245; 351/244; 248/280.1; 248/282; 248/419
[58] Field of Search ............... 351/245, 237, 239, 244; 248/145, 419, 184, 280.1, 282, 283

[56] References Cited

U.S. PATENT DOCUMENTS 4,116,548 9/1978 Persson ............................. 351/245
4,166,602 9/1979 Nilsen et al. ..................... 248/280.1

Primary Examiner—John K. Corbin
Assistant Examiner—Paul M. Dzierzynski

[57] ABSTRACT

The invention relates to a displacement system for opthalmologic examination units constituted of an instrument base section and an accessory section for mounting three ophthalmologic devices, said accessory section being connected by two lever means to said base section to enable displacement of the former relative to the latter from a first end position via an intermediate position into a second end position in the latter two positions relative to the said first end position the accessory section is displaced in parallel and at right angles relative to the base section so that the accessory section projects past over the base section. In this manner the opthalmologic devices are brought into an operation position in front of a patient and operator. A further lever system in combination with the lever means pivots a head rest to a patient in the intermediate and second end position, which head rest remains unchanged even when the ophthalmologic devices are changed for operation.

6 Claims, 3 Drawing Figures

DISPLACEMENT SYSTEM FOR AN OPTHALMOLOGIC EXAMINATION UNIT

The invention relates to a displacement system particularly for use in ophthalmological examination units constituted of a base section and an accessory section of the draw-out type extensible in parallel to the base member from a first end position via an intermediate position to a second end position projecting over the base member by means of a two lever gear means.

The inventional unit can be employed as a basic working place equipment for ophthalmologists, opticians and optometrists. In ophthalmologic examination bench units refractometers, ophthalmometers, and slit lamps are used, apart from auxiliary means for subjective refraction determination such as phoropters, eyeglass-testing sets and visual sign projectors.

The first mentioned devices are adjacently mounted upon an accessory section which is located above an instrument base section in a first end position and which permits sliding past a patient's seat perpendicular to the direction of sight of the patient so that subsequently all devices mounted on the accessory section are in operating position in front of the patient.

At the same time a head rest for the patient is brought in front of the patient and remains there even when the device is changed.

The head-rest is displaced in combination with the accessory section or by an additional straight-on guiding means.

Heretofore, the displacements of the accessory section in the course of changing the individual devices in front of the patient is almost entirely performed via straight-on guiding means as disclosed, for example, in the DE Utility model No. 6750992.

Previously, it has not been feasible to employ one and the same straight-on guiding means for displacing the bench plate from its rest position to the operation position of the first devices mounted thereupon, due to static and room problems.

This would require additional displacement members, such as disclosed in the firm's brochure A 52351d GG of Möller, Wedel, Optische Werke GmbH. In said brochure a second straight-on guiding means is shown in addition to pivots used. In the firm's brochure A 52355 d 1280 of the same firm a four-bar lever gear is disclosed.

Such solutions are disadvantageous since the two displacement members required increase the expenditures considerably, apart from the additional technical and operation expenditures involved due to arresting and releasing the individual independent displacement members.

In the event of the accessory section being pivoted into the operation position the operator has to move out of the way.

It is an object of the present invention, to obviate the above disadvantages.

It is a further object of the present invention to provide a displacement system for an accessory section for mounting ophthalmologic examination devices, which system does with only one guiding means.

It is still a further object of the invention to provide a displacement system and a head-rest being pivotally coupled to the former, for being swung in or out of an operation position.

These and other objects are realized in a displacement system for an ophthalmologic examination device in which an accessory section for mounting individual examination devices permits displacement from a first end position which is a non-operative position on an instrument base section into an intermediate (operative) position, and from there into a second (operative) end position along a substantially straight path.

In said intermediate position and said second end position the accessory section is projecting over said instrument base section at right angles to the first end position, and extends in front of a patient's seat.

The displacement of the accessory section is realized by two lever means which are hinged via their end portions to the base section and the accessory section, respectively.

In the first end position the two lever means are crossing one another, and in the intermediate position and in the second end position said two lever means are substantially in parallel to each other.

The four end points define four different distances, where the sum of the longest and shortest distance is greater than the sum of the two remaining distances.

The end position and the intermediate position of each of said levers is symmetrical to a plane which is at right angles to the pivoting plane of the lever means and in which the first ending point of the respective lever is situated. By virtue of the inventional lever arrangement an operator sitting in opposition to a patient needs not evade the movement of the accessory section when the latter is displaced from the first end position via an intermediate position, to the second end position, apart from the accessory section not being moved beyond those of the base section edge which is remote from the patient.

In the intermediate position a first of the ophthalmological devices mounted on the accessory section is in operation position in front of the patient.

In the second end position occupied after a substantially straight movement a second device is brought before the patient.

The second device and a third device are mounted upon a member seated upon the accessory section and permitting a rotation about 180° so that both devices can be mutually exchanged for operation.

When the accessory section is moved from the first end position into the intermediate position a head-rest is pivoted up to the patient, which maintains this position during further changes of the individual devices.

The head-rest is secured to a lever which is pivotally seated in the end point of the second lever at the base member and which is rigidly connected to one element of a three-bar lever.

The latter is arranged between the first end points of the two levers which connect the base section and the accessory section in such a manner that members of the three-bar-lever which are adjacent the first end point of the first lever are in one line in the pivoting range between the intermediate position and the second end position. The members of the three-bar-lever which are adjacent the first end point of the second lever include an acute angle.

When the accessory section is pivoted from the intermediate position into the first end position, the hinge between the members of the three-bar-lever adjacent the first end point of the first lever is bent and thus the head-rest turned off the patient.

Figure 2:
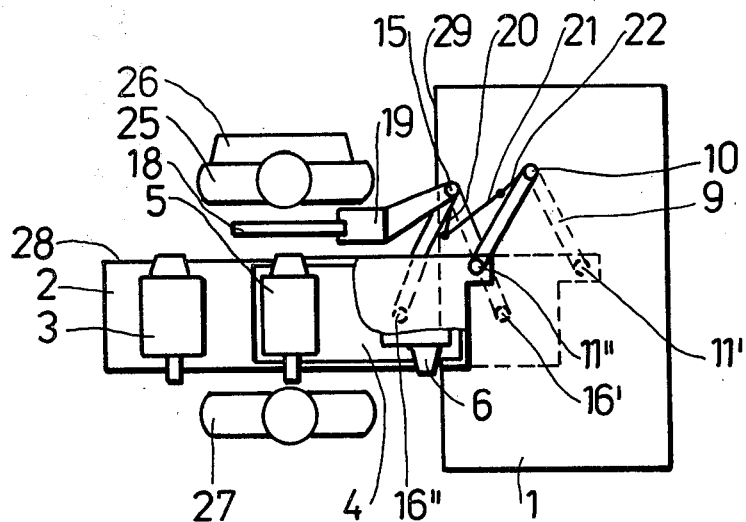
Figure 3:
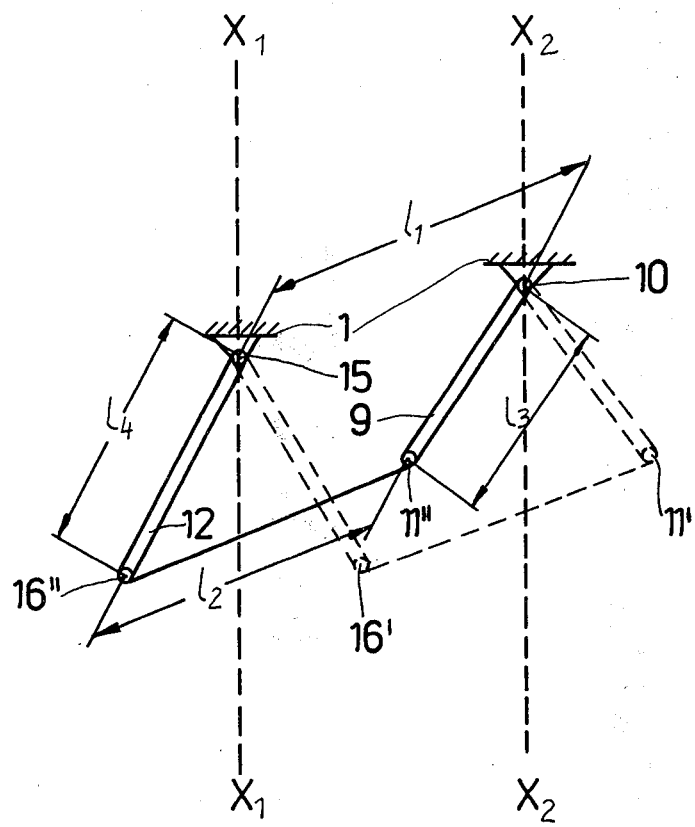

In order that the invention may be more readily understood reference is made to the accompanying drawings which illustrate diagrammatically and by way of example one embodiment thereof and where FIG. 1 is a schematic view of a displacement system for a diagnostic unit including an accessory section in a first end position, FIG. 2 is a schematic view of the diagnostic unit of FIG. 1, however, having the accessory section in a second end position, and FIG. 3 is a schematic view for demonstrating the lever efficient forces of said diagnostic unit.

In FIG. 1 a diagnostic unit comprises a base section 1 having a top face upon which an accessory section 2 is mounted via a bottom face of the latter.

The accessory section 2 is in a first end position, having a leading edge 29 substantially in parallel to a leading edge 28 of the base section 1.

A first ophthalmologic device 3 is mounted on said accessory section 2 and a second and third ophthalmologic device 5 and 6 is mounted on a mounting plate 4 which is, in turn, rotatably seated upon said accessory section 2 for 180° rotations. A first lever 9 is hinged to said base section 1 via a first end portion 10 and to the accessory section via the second end portion 11.

A second lever 12 is hinged via a first end portion 15 to the base section 1 and to the accessory section 2 via a second end portion 16.

A lever 19 carries a head-rest 18. Said lever 19 is seated for rotation in the base section 1 at the first end point 15 of the second lever 12 and is rigidly connected to a mamber 20 of a three-bar-lever constituted of the members 20, 21 and 22.

The member 20 of the three-bar-lever is pivotally seated at the first end portion 10 of the first lever 9. A patient 25 is seated in a patient's seat 26 in opposition to an operator 27, for example, an ophthalmologist.

In FIG. 2 the diagnostic unit is in an operational state, that is, the accessory section 2 has been displaced to a second end position in which the leading edges 28, 29 are at right angles to each other.

The second (operative) ophthalmologic device 5 is located between the operator 26 and the patient 27. An intermediate position of the accessory section 2 is also represented in FIG. 2 by the dashed lines, which show a portion of the accessory section 2, the first lever 9 and the second lever 12.

The head-rest 18 is positioned in front of the patient 25. In operation, the accessory section 2 is moved from the first end position (FIG. 1) into an intermediate position (dashed lines of FIG. 2), in the course of said operation the first lever 9 is rotated about its ending point 10 hinged to the base section 1 and the second lever 12 about its ending point 15, also hinged to the base section 1.

By said movement about the points 10 and 15 the accessory section moves past both, the operator 26 and the patient 27 without the necessity for any of the two to move out of position.

At the same time, the member 22 of the three-bar-lever pivots about the first ending point 10 of the first lever 9 towards the patient and, by a co-motion of the members 20, 21 and the lever 19 the head rest 18 is brought in front of the patient 25.

When placing the accessory section 2 into the second end position (FIG. 2) the second device 5 is positioned in front of the patient 25 the lever 19 and the members 20, 21, 22 maintain their previous position and so does the head-rest 18.

The third ophthalmologic device 6 is positioned in front of the patient 25 as follows.

The mount plate 4 is rotated about 180° on the accessory section 2 when the latter is in the intermediate position and subsequently, the accessory section 2 is moved into the second end-position.

The movements of the diagnostics unit and of the individual devices 3, 5 and 6, respectively, are effected manually. To this end any suitable means (not shown) are provided at the respective sections.

In FIG. 3 only the lever means 9 and 12 are shown in the second end position of the accessory section 2 relative to the base-section 1 and in the intermediate position (shown in dashed lines). The first end points 10 and 15 of the levers 9 and 12, respectively have a distance $l_1$ from one another, and are seated for rotation in respective seating means (not shown) of the non-displaceable base-section 1.

The end points 11" and 16" of the first and second lever means 9 and 12, respectively, have a distance of $l_2$ from one another and are seated for rotation in respective seating means of the accessory section 2 (not shown) which effects the coupling of the levers 9, 12. A distance $l_3$ between the points 10 and 11", (11') of the first lever 9 and a distance $l_4$ between the points 15 and 16" (16' in the intermediate position) of the second lever 12 represent the efficient lever arms. The distances $l_1$, $l_2$, $l_3$, $l_4$ are so selected that the end points 16" and 16', and 11" and 11' defining the second end position relative to the intermediate position are symmetrical to a plane of symmetry $x_1-x_1$ and $x_2-x_2$, respectively, which is at right angles to the drawing plane and the end points 10 and 15 are located in the respective plane of symmetry $x_1-x_1$, $x_2-x_2$.

Furthermore the sum of the longest and shortest distance of $l_1$, $l_2$, $l_3$, $l_4$ is greater than the sum of the two remaining distances. Thus, when, for example $l_1 > l_2$, $l_2 > l_3$ and $l_3 > l_4$ then $l_1$ plug $l_4 > l_2$ plus $l_3$.

The inventional lever system is, of course, not restricted to said example. Any other combination of $l_1$ to $l_4$ satisfying the above term lies within the scope of the invention.

We claim:

1. A displacement system for an ophthalmologic examination unit particularly for use in ophthalmologic examinations for displacing a base section relative to an accessory section, comprising the base section having a top face and a leading edge,
the accessory section for mounting at least two ophthalmologic devices,
said accessory section having a bottom face and a leading edge,
said base section top face and
said accessory section bottom face being substantially in parallel opposition to each other at a spaced relation,
a first lever means having a first end point and a second end point,
a second lever means having a third end point and a fourth end point,
said first lever means and said second lever means being arranged between said top face and said bottom face substantially in planes parallel to the former and the latter,
a first seating means, and a second seating means being provided at said top face of said base section, a third and a fourth seating means being provided at said bottom face of said accessory section, said first lever means being connected via said first end point to said first seating means for rotation about the latter in one of said planes, and being connected via said second end point to said third seating means for rotations about the latter in said one of said planes, said second lever means being connected via said third end point to said second seating means for rotations about the latter in the other of said planes, and being connected via said fourth end point to said fourth seating means for rotations about the latter in said other of said planes, said first lever means and said second lever means being for displacing said accessory section relative to said base section, said first lever means and said second lever means being crosswise arranged in a first end position of said accessory section relative to said base section, and being substantially in parallel to each other in an intermediate position and a second end position, respectively, of said accessory section relative to said base section, said first end point and said third end point having a first distance, said second end point and said fourth end point having a second distance, said first end point and said second end point having a third distance, said third end point and said fourth end point having a fourth distance, said first, second, third and fourth distance being different from each other, the sum of the greatest of the distances and the shortest of said distances is greater than the sum of the remaining distances.

2. A displacement system as claimed in claim 1, wherein said accessory section and said base section having their leading edges in parallel to each other in said first end position and having said leading edges at right angles to each other in parallel to said planes in said intermediate position and said second end position, respectively, said accessory section projecting over said base section in said intermediate position and said second end position.

3. A displacement system as claimed in claim 2, wherein the positions of said first lever means and said second lever means, respectively, in said intermediate position relative to the position of said first and second lever means, respectively, in said second end position are symmetrical to respective planes of symmetry which are at right angles to said planes and in parallel to the leading edge of said accessory section in said intermediate and second end position, and wherein the first end point and said third end point, respectively, lies in the respective plane of symmetry.

4. A displacement system as claimed in claim 3, wherein a three-bar-lever is provided constituted of three subsequent members, the first member being connected to said first end point, the third member being connected to said third end point, the second member being hinged via its end portions to said first and said second member, and wherein in said intermediate position and second end position, said first and said second member forming a straight line, and second and third member including an acute angle, and wherein a further lever being pivotaly connected to said third end point and rigidly connected to said third member, said further lever being pivotally in parallel to said respective planes.

5. A displacement system as claimed in claim 4, wherein said further lever is provided with a head-rest.

6. A displacement system as claimed in claim 5, wherein a mount plate is seated for 180° rotation on and relative to said accessory section in parallel to the latter about a central pivot, said mount plate mounting two ophthalmologic devices.

* * * * *